(12) United States Patent
Dong et al.

(10) Patent No.: US 12,077,494 B2
(45) Date of Patent: Sep. 3, 2024

(54) ALKOXYCARBONYLATION OF TRIVINYLCYCLOHEXANE

(71) Applicant: EVONIK OPERATIONS GMBH, Essen (DE)

(72) Inventors: Kaiwu Dong, Bo Zhou (CN); Robert Franke, Marl (DE); Ralf Jackstell, Rostock (DE); Matthias Beller, Ostseebad Nienhagen (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 0 days.

(21) Appl. No.: 18/179,456

(22) Filed: Mar. 7, 2023

(65) Prior Publication Data

US 2023/0219877 A1 Jul. 13, 2023

Related U.S. Application Data

(63) Continuation of application No. 17/122,187, filed on Dec. 15, 2020, now Pat. No. 11,629,115.

(30) Foreign Application Priority Data

Dec. 17, 2019 (EP) .................................. 19216884

(51) Int. Cl.
| | | |
|---|---|---|
| C07C 69/608 | (2006.01) | |
| B01J 31/22 | (2006.01) | |
| C07C 67/36 | (2006.01) | |
| C07C 67/38 | (2006.01) | |
| C07C 67/40 | (2006.01) | |
| C08K 5/12 | (2006.01) | |
| C07C 69/003 | (2006.01) | |

(52) U.S. Cl.
CPC ......... *C07C 69/608* (2013.01); *B01J 31/2295* (2013.01); *C07C 67/36* (2013.01); *C07C 67/38* (2013.01); *C07C 67/40* (2013.01); *C08K 5/12* (2013.01); *B01J 2531/824* (2013.01); *C07C 69/003* (2013.01)

(58) Field of Classification Search
CPC ......... C07C 67/36; C07C 67/38; C07C 67/40; C07C 69/74; C07C 69/608; C08K 5/12
See application file for complete search history.

(56) References Cited

U.S. PATENT DOCUMENTS

| 5,153,354 | A | * | 10/1992 | Schroder ................. C07C 67/38 560/114 |
|---|---|---|---|---|
| 8,344,187 | B2 | | 1/2013 | Ikariya et al. |
| 10,562,838 | B2 | | 2/2020 | Fang et al. |
| 2017/0022137 | A1 | | 1/2017 | Dong et al. |
| 2017/0022236 | A1 | | 1/2017 | Dong et al. |
| 2018/0022686 | A1 | | 1/2018 | Fang et al. |
| 2019/0194113 | A1 | | 6/2019 | Sang et al. |
| 2021/0179534 | A1 | | 6/2021 | Schulz et al. |

FOREIGN PATENT DOCUMENTS

| CN | 102089266 A | 6/2011 |
|---|---|---|
| CN | 106432365 A | 2/2017 |
| CN | 107628952 A | 1/2018 |
| EP | 0 495 175 A2 | 7/1992 |
| EP | 3 272 733 A1 | 1/2018 |

OTHER PUBLICATIONS

European Search Report dated Jun. 4, 2020 in Patent Application No. 19216884.7 (7 pages in German).
Singapore Search Report dated Sep. 1, 2021 for Singapore Patent Application No. 10202012353Q (2 pages).
Examination Report dated Oct. 7, 2021 for Patent Office of the Cooperation Council for the Arab States of the Gulf (GCC) No. 2020-41133 (5 pages).
Examination Report dated Feb. 2, 2023 for Indian Patent Application No. 202014054486 (5 pages).
Brennfuher, A., et al., Palladium-catalyzed carbonylaiton reactions of alkenes and alkynes, ChemCatChem. 2009. vol. 1, pp. 28-41.
First Office Action mailed Dec. 11, 2023 for Chinese Patent Application No. 202011488750.X (8 pages in Chinese; 8 pages English Translation).
Yao, Qingwei. Ruthenium, carbonyl[2-(diphenylphosphino-κP)-N-[2-(diphenylphosphino-κP)ethyl]ethanamine-κN][tetrahydroborato (1-)-κH]-hydrido, (OC-6-13)-. In Encyclopedia of Reagents for Organic Synthesis. 2015. https://doi.org/10.1002/047084289X.rn01801. 3 pages.

\* cited by examiner

*Primary Examiner* — Yate' K Cutliff
(74) *Attorney, Agent, or Firm* — Smith, Gambrell & Russell, LLP

(57) ABSTRACT

Process for the alkoxycarbonylation of trivinylcyclohexane.

2 Claims, No Drawings

ALKOXYCARBONYLATION OF TRIVINYLCYCLOHEXANE

The present invention relates to a process for the alkoxycarbonylation of trivinylcyclohexane.

The alkoxycarbonylation of ethylenically unsaturated compounds is a process of increasing significance. An alkoxycarbonylation is understood to mean the reaction of ethylenically unsaturated compounds such as olefins with carbon monoxide and alcohols in the presence of a metal or a metal complex and a ligand to give the corresponding esters:

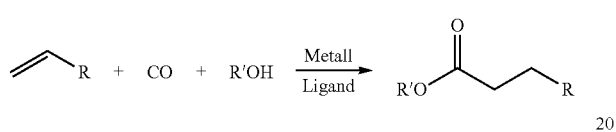

The problem addressed by the present invention was that of providing a process for the alkoxycarbonylation of trivinylcyclohexane. All three vinyl groups can be converted into esters using this process.

In addition, a rapidly gelling plasticizer for plastics, especially for PVC, is intended to be provided which enables a low processing temperature.

This object is achieved by a process according to the process below.

Process comprising the process steps of:

a) initially charging one of the compounds (i), (ii), (iii) or a mixture of at least two of these compounds:

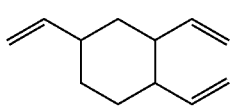
(i)

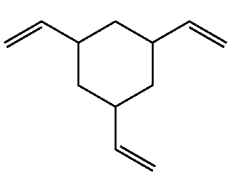
(ii)

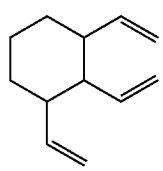
(iii)

b) adding the ligand (L) and a compound comprising Pd, or adding a complex comprising Pd and the ligand (L):

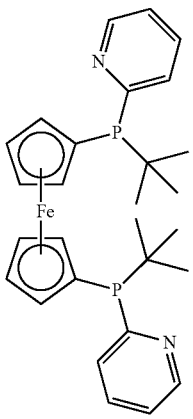
(L)

c) adding an alcohol having 1 to 12 carbon atoms;
d) feeding in CO;
e) heating the reaction mixture of a) to d), wherein the compound/the mixture of a) is converted to a triester.

In one variant of the process, the compound (i) is initially charged in process step a).

In one variant of the process, the compound (ii) is initially charged in process step a).

In one variant of the process, the alcohol in process step c), besides the oxygen, does not comprise any further heteroatoms and contains no multiple bonds.

In one variant of the process, the alcohol in process step c) is selected from: methanol, ethanol, $^n$butanol, methylpropanol, $^n$pentanol, $^{iso}$pentanol, 2-methylbutanol, 3-methylbutanol, $^n$hexanol, $^{iso}$hexanol, $^n$heptanol, $^{iso}$heptanol, $^n$octanol, $^{iso}$octanol, 2-ethylhexanol, $^n$nonanol, $^{iso}$nonanol, $^n$decanol, $^{iso}$decanol, 2-propylheptanol.

In one variant of the process, the alcohol in process step c) is methanol.

In one variant of the process, CO is fed in in process step d) up to a pressure in the range from 20 bar to 60 bar.

In one variant of the process, CO is fed in in process step d) up to a pressure in the range from 30 bar to 50 bar.

In one variant of the process, the heating in process step e) is carried out at a temperature in the range from 90° C. to 130° C.

In one variant of the process, the heating in process step e) is carried out at a temperature in the range from 100° C. to 120° C.

In one variant of the process, this process comprises the additional process step f):

f) purifying the triester.

In one variant of the process, this process comprises the additional process step g):

g) reacting the purified triester with NaOMe and $H_2$ to give the triol.

In one variant of the process, the reaction in process step g) is catalyzed with Ru-MACHO-BH.

In one variant of the process, the reaction in process step g) is carried out at a $H_2$ pressure in the range of 30 bar to 70 bar.

In one variant of the process, the reaction in process step g) is carried out at a $H_2$ pressure in the range of 40 bar to 60 bar.

In one variant of the process, the reaction in process step g) is carried out at a temperature in the range from 80° C. to 120° C.

In one variant of the process, the reaction in process step g) is carried out at a temperature in the range from 90° C. to 110° C.

In addition to the process, a compound is also claimed.
Compound according to the formula (1):

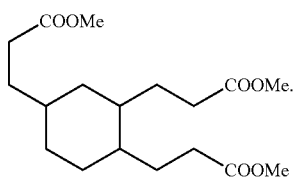

The compound is preferably prepared according to the process described herein.

Compound prepared by the process described above.

The invention is to be illustrated in detail hereinafter by a working example.

Synthesis of trimethyl 3,3',3"-(cyclohexane-1,2,4-triyl)tripropionate (1) ("triester")

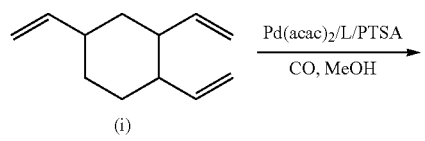

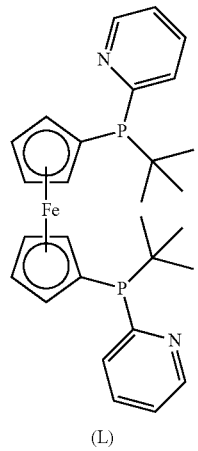

[Pd(acac)$_2$] (15.2 mg, 0.1 mol %), L (103 mg, 0.4 mol %) and para-toluenesulfonic acid (PTSA, 143 mg, 1.5 mol %) were placed in a 100 ml steel autoclave under an argon atmosphere. Then, MeOH (30 ml) and trivinylcyclohexane (i) (8.1 g, 50 mmol) were injected by syringe. The autoclave was flushed three times with CO and then pressurized at a CO pressure of 40 bar. The reaction was carried out at 110° C. over 10 h. Subsequently, the autoclave was cooled down to room temperature and decompressed. The desired product was purified by distillation (165° C. at 10$^{-3}$ bar) and characterized by $^1$H—, $^{13}$C-NMR and HR-MS (15.6 g, 91% yield).

$^1$H-NMR (300 MHz, C$_6$D$_6$) δ=3.39-3.37 (m, 9H), 2.24-1.86 (m, 7H), 1.48-0.27 (m, 14 H). $^{13}$C-NMR (75 MHz, C$_6$D$_6$) δ=173.68-173.54 (m), 51.04, 40.60-40.47 (m), 38.24, 38.14, 37.51, 37.07, 36.54, 36.10, 35.52, 35.14, 33.87, 32.70, 32.55, 32.51, 32.38, 32.29, 32.23, 32.08, 31.97, 31.86, 31.76, 31.68, 31.63, 31.43, 30.98, 30.79, 30.75, 29.31, 28.52, 28.47, 28.34, 28.13, 28.11, 27.13, 26.58, 25.12, 20.79, 19.74.

MS (EI): 311 (13.40), 293 (3.65), 269 (75.76), 237 (60.40), 219 (25.13), 205 (100), 191 (17.62), 177 (14.83), 145 (24.59).

HR-MS (ESI): Calculated C$_{18}$H$_{30}$O$_6$ [M+H]$^+$: 343.21152, found: 343.21113.

Synthesis of 3,3',3"-(cyclohexane-1,2,4-triyl)tris(propan-1-ol) (2) ("triol")

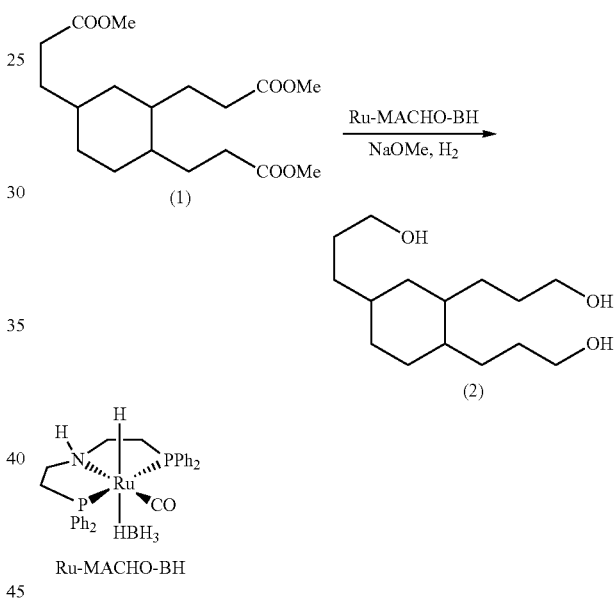

Ru-MACHO-BH (59 mg, 2 mol %) and NaOMe (27 mg, 10 mol %) were placed in a 25 ml steel autoclave under an argon atmosphere. Then, MeOH (8 ml) and the triester (1) (1.93 g, 5.67 mmol) were injected by syringe. The autoclave was flushed three times with H$_2$ and then pressurized at a H$_2$ pressure of 50 bar. The reaction was carried out at 100° C. over 10 h. The autoclave was then cooled to room temperature and decompressed. The desired product was purified by filtration over silica gel and characterized by $^1$H—, $^{13}$C-NMR and HR-MS (1.4 g, 96% yield).

$^1$H-NMR (400 MHz, CD$_3$OD) δ=3.32-3.30 (m, 6H), 1.85-1.77 (m, 2H), 1.63-0.62 (m, 19 H). $^{13}$C-NMR (100 MHz, CD$_3$OD) δ=63.53-63.29 (m), 42.69, 42.53, 42.39, 42.31, 40.34, 40.24, 39.28, 38.89, 38.12, 38.02, 37.58, 37.27, 35.89, 34.78, 34.72, 34.53, 34.37, 33.17, 31.52, 31.50, 31.40, 31.38, 31.05, 30.60, 30.48, 30.41, 30.32, 30.24, 30.17, 28.77, 28.22, 26.61, 22.53, 21.45. MS (EI): 222 (1.06), 194 (1.14), 181 (2.96), 163 (11.54), 135 (9.81), 121 (17.04), 107 (15.25), 93 (32.69).

HR-MS (ESI): Calculated C$_{15}$H$_{30}$O$_3$ [M+H]$^+$: 259.22677, found: 259.2269.

Production of Plastisols

PVC plastisols were produced, as used, for example, for the manufacture of topcoat films for floor coverings. The figures in the plastisol formulation are each in parts by mass. The formulation of the polymer composition is listed in Table 1.

TABLE 1

| Plastisol formulation | |
|---|---|
| | phr |
| PVC (Vestolit B 7021 - Ultra; from Vestolit) | 100 |
| Plasticizer | 50 |
| Epoxidized soybean oil as costabilizer (Drapex 39, from Galata) | 3 |
| Thermal stabilizer based on Ca/Zn (Reagent CLX/759/6PF) | 2 |

Figures in phr (phr = parts per hundred parts resin)

First the liquid constituents and then the pulverulent constituents are weighed out into a PE beaker. The mixture is stirred manually with an ointment spatula in such a way that no unwetted powder is present any longer. The mixing beaker is then clamped into the clamping device of a dissolver stirrer. After switching on the stirrer, the speed is slowly increased to ca. 2000 rpm. Meanwhile, the plastisol is carefully deaerated, the pressure being kept below 20 mbar.

As soon as the plastisol has reached a temperature of ca. 30° C., the speed is lowered to ca. 350 rpm. Henceforth, the plastisol is deaerated for 9 minutes at this speed and a pressure below 20 mbar. This ensured that the plastisol was homogenized with a defined energy input. Thereafter, the plastisol is immediately equilibrated to 25.0° C. in a climate-controlled cabinet for further studies.

Gelation Characteristics of the Plastisols

The gelation characteristics of the pastes were examined with a Physica MCR 101 in oscillation mode using a parallel plate analysis system (PP25), which was operated under shear stress control. An additional heating hood was connected to the system in order to achieve a homogeneous heat distribution and uniform sample temperature.

The following parameters were set:
Mode: Temperature gradient
Start temperature 25° C.
End temperature 180° C.
Heating/cooling rate 5° C./min
Oscillation frequency 4-0.1 Hz logarithmic ramp
Cycle frequency omega: 10 1/s
Number of measurement points: 63
Measurement point duration: 0.5 min
Automatic gap adjustment F: 0 N
Constant Measurement Point Duration
Gap width 0.5 mm Analysis Procedure:

The spatula is used to apply a few grams of the paste to be analysed, free from air bubbles, to the lower plate of the analysis system. In doing so, it is ensured that, after the analysis system had been assembled, it is possible for some paste to exude uniformly out of the analysis system (not more than 6 mm in any direction). The heating hood is subsequently positioned over the sample and the analysis is started. The complex viscosity of the paste is determined after 24 h (storage of the paste at 25° C. in a temperature control cabinet from Memmert) as a function of temperature.

A distinct rise in the complex viscosity is considered to be a measure of gelation. The comparative value used is therefore the temperature on attainment of a paste viscosity of 1000 Pas.

The experiment was repeated with three comparative plastisols in which another plasticizer was used in each case.

TABLE 2

Gelling of the plastisols after 24 h, temperature in ° C. on attainment of a paste viscosity of $10^3$ Pa · s:

| Experiment | Plasticizer | Gelling temperature [° C.] |
|---|---|---|
| 1* | Trimethyl 3,3',3''-(cyclohexane-1,2,4-triyl)tripropionate (1) | 65 |
| 2 | Diisononyl phthalate (DINP), VESTINOL 9 from Evonik Performance Materials GmbH | 83 |
| 3 | Diisononyl 1,2-cyclohexanedicarboxylate (DINCH), ELATUR CH from Evonik Performance Materials GmbH | 101 |
| 4 | Diisopentyl terephthalate (DPT), ELATUR DPT from Evonik Performance Materials GmbH | 70 |

*experiment with inventive compound

The target value of 1000 Pa*s could already be achieved with the compound (1) according to the invention at 65° C. Such low gelling temperatures are advantageous for the processing procedure. They enable plastisol processing at lower temperatures.

The invention claimed is:

1. Compound according to the formula (1):

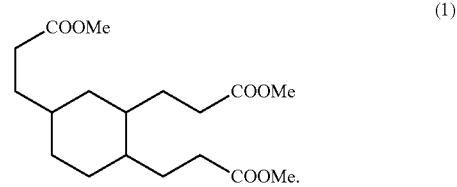 [SMILES: COC(=O)CCC1CCC(CCC(=O)OC)C(CCC(=O)OC)C1]

(1)

2. In a plastisol mixture including a plasticizer wherein the improvement comprises the compound of claim 1.

* * * * *